United States Patent [19]

Tanimoto

[11] 4,388,722
[45] Jun. 14, 1983

[54] AUTOMATIC CLEANING DEVICE FOR USE IN AN EXTRACTING FURNACE OF AN APPARATUS FOR ANALYZING GASES IN METALS

[75] Inventor: Masahiro Tanimoto, Kyoto, Japan

[73] Assignee: Horiba, Ltd., Kyoto, Japan

[21] Appl. No.: 274,370

[22] Filed: Jun. 17, 1981

[30] Foreign Application Priority Data

Jul. 5, 1980 [JP] Japan .................................. 55-91989

[51] Int. Cl.$^3$ ............................................... H05B 3/00
[52] U.S. Cl. ........................................ 373/118; 73/19; 219/427
[58] Field of Search ....................... 373/118; 219/427; 73/19; 250/281, 289

[56] References Cited

U.S. PATENT DOCUMENTS

| | | | |
|---|---|---|---|
| 3,899,627 | 8/1975 | Sitek et al. | 219/427 |
| 3,946,228 | 3/1976 | Biermann | 73/19 |
| 4,056,677 | 11/1977 | Berk et al. | |

Primary Examiner—Roy N. Envall, Jr.
Attorney, Agent, or Firm—Wenderoth, Lind & Ponack

[57] ABSTRACT

An automatic cleaning device is employed in an extracting furnace of an apparatus for analyzing gases in metals, the furnace including upper and lower electrodes relatively movable between a closed position, whereat a crucible containing a sample to be analyzed may be contacted and heated by the electrodes, and an open position, whereat the electrodes are spaced from each other. The automatic cleaning device cleans the upper and lower electrodes and includes a support bracket mounted for movement laterally of the electrodes. A cleaning unit is supported on the support bracket and is movable thereby between a first position located laterally of the electrodes and a second position located between the electrodes. The cleaning unit includes a crucible removal device to remove a spent crucible from the electrodes upon movement of the cleaning unit to the second position thereof. The cleaning unit includes upper and lower brushes rotatable to clean the upper and lower electrodes. The cleaning unit is mounted on the support bracket for vertical movement relative thereto. Thus, when the cleaning unit is in the second position thereof, relative movement between the upper and lower electrodes toward the closed position thereof causes the cleaning unit to be moved vertically until the upper and lower cleaning brushes are contacted with and clean the upper and lower electrodes.

27 Claims, 11 Drawing Figures

AUTOMATIC CLEANING DEVICE FOR USE IN AN EXTRACTING FURNACE OF AN APPARATUS FOR ANALYZING GASES IN METALS

BACKGROUND OF THE INVENTION

The present invention is directed to an automatic cleaning device for use in an extracting furnace of an apparatus for analyzing gases, particularly nitrogen, oxygen, hydrogen and the like, contained in metals.

The present invention is more particularly directed to such an automatic cleaning device which is capable of saving manual labor required to clean an extracting furnace of the direct heating type in which a crucible containing a metal sample is held between upper and lower electrodes and resistance heated, whereby gases contained in a metal sample within the crucible are extracted and directed to a gas analyzing apparatus.

In the use of such systems, it is necessary to clean the interior of the extracting furnace after every gas analyzing operation because the inside surfaces of the extracting furnace become stained due to sudden boiling of the molten metal sample, sublimination of the crucible and the like. In the past, such cleaning has been carried out manually. However, manual cleaning is inherently inefficient, particularly when from 100 to 200 cleaning operations per day must be carried out. This is further particularly true, when the extracting furnace is normally located in an iron or steel plant wherein the environment is not conducive to thoroughly precise and repetitive cleaning operations. Additionally, there are likely to occur different qualities or degrees of cleaning of the interior of the extracting furnace due to different persons conducting cleaning operations. This results in different degrees of cleaning of electrode surfaces, thereby resulting in varying contact resistance between the crucible and electrodes. This alters the extraction efficiency, which can influence the results of the following analyses. Even further, soot-like dust is generated during the cleaning of the interior of the extraction furnace and such dust not only soils the apparatus but also the surrounding environment. This necessitates that the workers must wear masks.

SUMMARY OF THE INVENTION

With the above discussion in mind, it is the object of the present invention to provide an automatic cleaning device for use in an extracting furnace of an apparatus for analyzing gases in metals, whereby the above and other prior art disadvantages are overcome.

It is a further object of the present invention to provide such an automatic cleaning device which is simple in construction and efficient in operation.

It is an even further object of the present invention to provide an extracting furnace employing such automatic cleaning device.

The above objects are achieved in accordance with the present invention by the provision, in an extracting furnace for use with a gas analyzing device, the furnace being of the type including upper and lower electrodes relatively movable between a closed position, whereat a crucible containing a sample to be analyzed may be contacted and resistance heated by the electrodes, and an open position, whereat the upper and lower electrodes are spaced from each other, an automatic device for cleaning the upper and lower electrodes when such electrodes are in the open position thereof. The cleaning device includes a support bracket mounted for movement laterally of the electrodes. A cleaning unit is supported on the support bracket and is movable thereby between a first position located laterally of the electrodes and a second position located between the electrodes. A crucible removal device is located on the cleaning unit to remove a spent crucible from the electrodes upon movement of the cleaning unit to the second position thereof. The cleaning unit includes upper and lower cleaning elements, preferably brushes, operable for cleaning the upper and lower electrodes. The cleaning unit is mounted on the support bracket for vertical movement relative thereto, such that when the cleaning unit is in the second position thereof, relative movement between the upper and lower electrodes toward the closed position thereof moves the cleaning unit vertically until the upper and lower cleaning elements are contacted with and clean the upper and lower electrodes.

In accordance with a further feature of the present invention the cleaning device includes an arrangement for removing dust generating during cleaning of the upper and lower electrodes. Such dust removing arrangement includes conduits adapted to be connected to a suction source and opening into areas above and below the cleaning unit. The upper and lower electrodes have extending therefrom flanges contacting the cleaning unit, thereby forming upper and lower closed chambers. The suction conduits extend through the cleaning unit and open into the upper and lower chambers.

The upper and lower electrodes preferably have respective inner electrode surfaces adapted to contact the crucible, and the upper and lower brushes are adapted to rotate against the respective electrode surfaces. The automatic cleaning device of the invention includes a structure for rotating the brushes. The cleaning unit includes a gear block, and the rotating structure includes a vertically extending spindle journalled for rotation in the gear block and supporting at opposite ends thereof the brushes. The spindle has fixed thereto a first gear, such as a worm gear. A horizontally extending shaft is journalled for rotation in the gear block and is adapted to be connected to a power source for rotation thereof. The shaft has fixed thereto a second gear, such as a worm gear, meshing with the first gear. Preferably, the upper and lower brushes are removably and interchangeably threaded onto opposite ends of the vertical spindle.

The support bracket is preferably slidably mounted on at least one horizontally extending guide bar, and a device, such as an air or hydraulic cylinder is mounted on the furnace and connected to the support bracket for moving the support bracket toward and away from the electrodes. Preferably the upper electrode is fixed and the lower electrode is vertically movable toward and away from the upper electrode toward the closed and opened positions. The cleaning unit is slidably mounted on at least one vertically extending guide bar which is fixedly mounted on the support bracket. Springs are mounted on the vertically extending guide bars for urging the cleaning unit downwardly. When the lower electrode is moved upwardly toward the upper electrode, and when the cleaning unit is in the second position thereof, the lower electrode moves the cleaning unit upwardly along the vertically extending guide bars, against the downwardly urging force of the springs.

The crucible removal device may take numerous forms, but preferably includes a crucible holder mounted on the cleaning unit, the holder having a concave surface substantially corresponding to the exterior profile of a crucible employed, and conduits, adapted to be connected to a suction source, opening into the concave surface. Such conduits preferably extend through the cleaning unit.

BRIEF DESCRIPTION OF THE DRAWINGS

Other objects, features and advantages of the present invention will become apparent from the following detailed description, taken with the accompanying drawings, wherein.

DETAILED DESCRIPTION OF THE INVENTION

Figure 1:
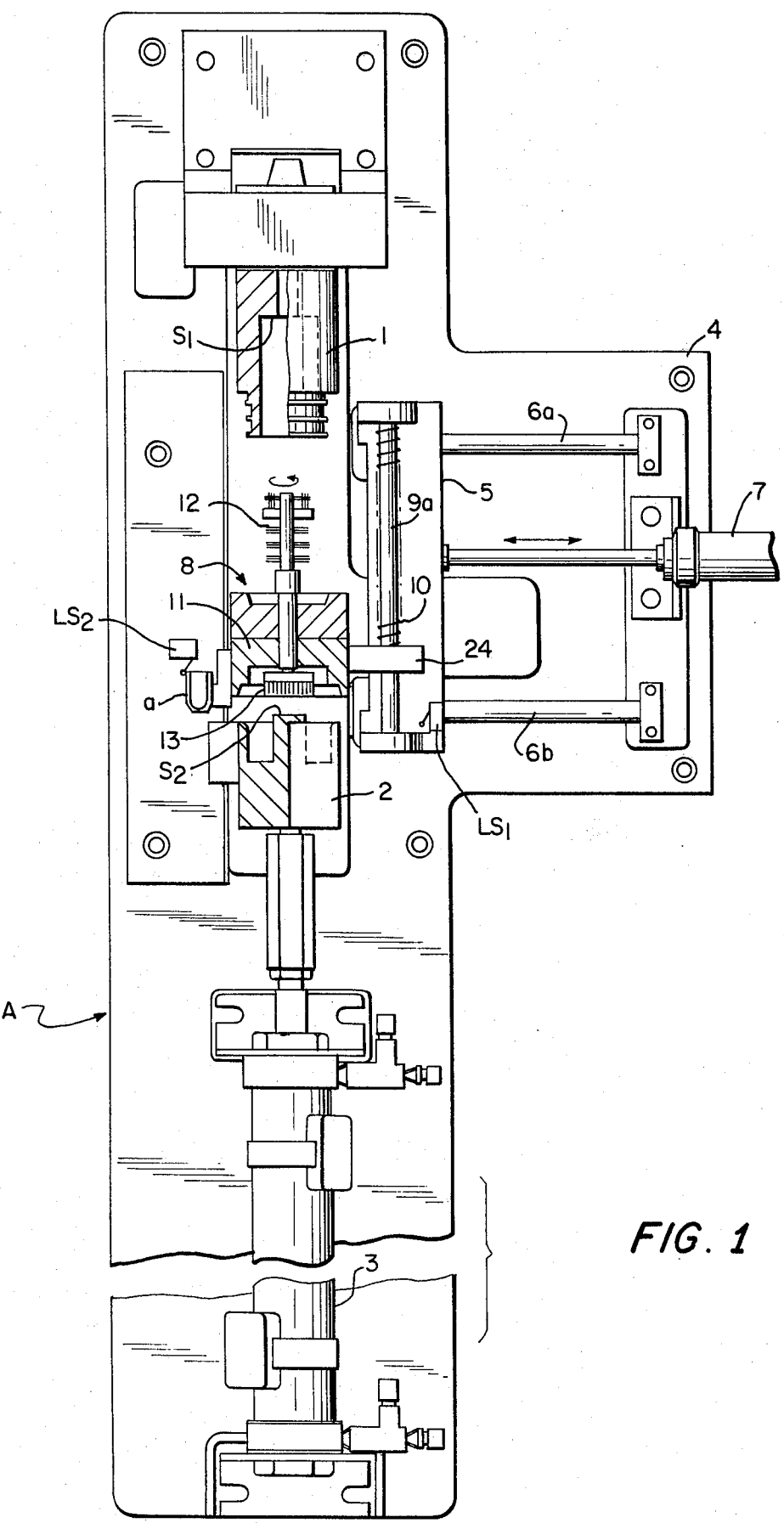
FIG. 1 is a front view, partially in section, of an extracting furnace including an automatic cleaning device according to the present invention.
Figure 3:
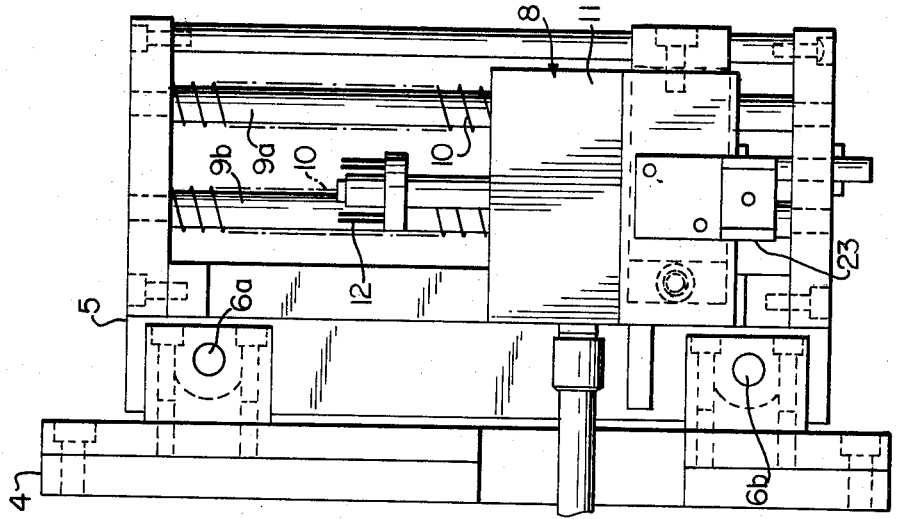
FIG. 3 is a side view, viewed from the left side of FIG. 2.
Figure 2:
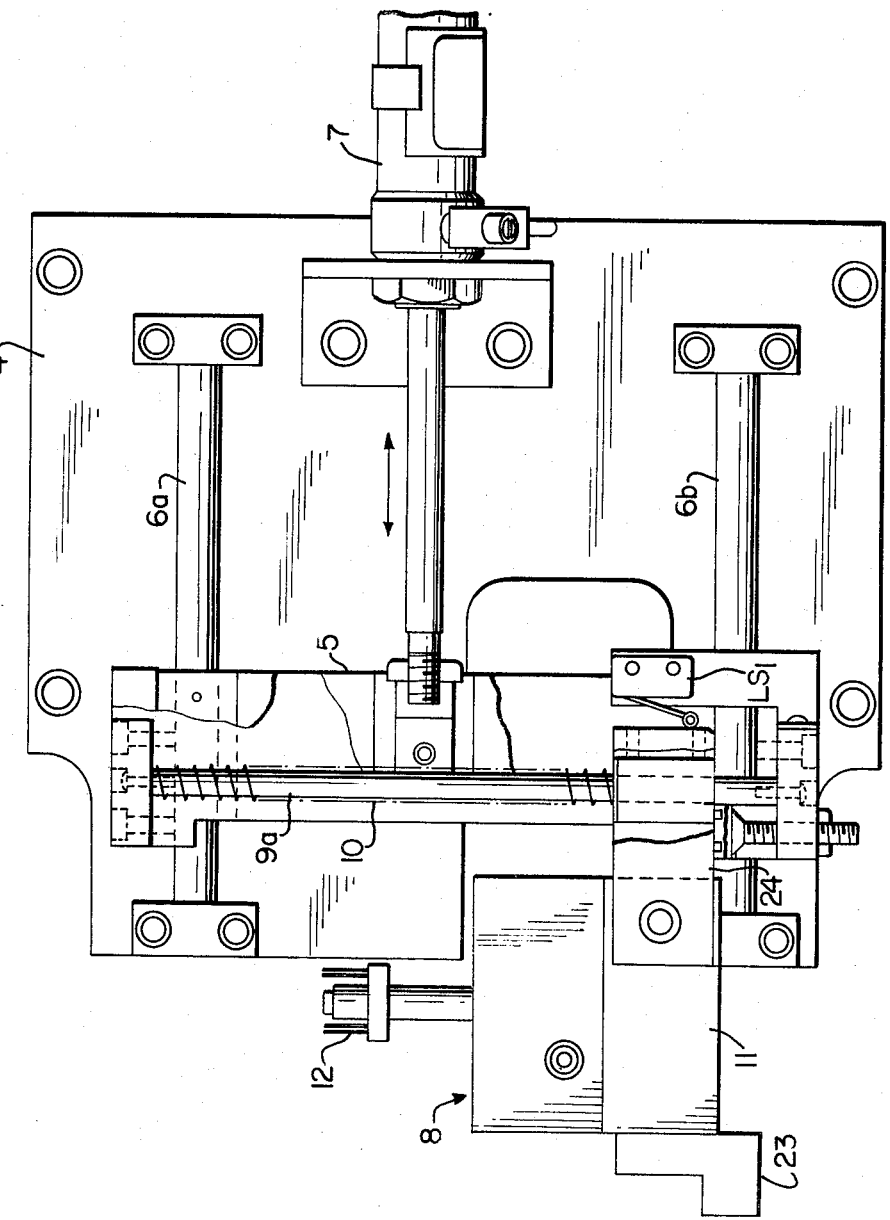
FIG. 2 is a front view, on an enlarged scale, of the cleaning device.

In FIG. 1 there is illustrated a complete extracting furnace of the type employed in an apparatus for analyzing gases in metals. The extracting furnace includes a housing A having fixingly mounted thereon an upper electrode 1. A lower electrode 2 is mounted for vertical movement on housing A, for example by means of hydraulic or air cylinder 3. During normal use of the extracting furnace a crucible a containing a metal sample is positioned on electrode surface $S_2$ of lower electrode 2. Lower electrode 2 is then moved upwardly from the open position shown in FIG. 1 to a closed position whereat the top of crucible a contacts an electrode surface $S_1$ of upper electrode 1. In a conventional manner, the electrodes are electrified such that crucible a and the metal sample contained therein are heated by resistance heating. The metal sample is made molten, and gases generated are transported to a gas analyzer by means of an inert carrier gas.

Upon completion of such analyzing operation, the lower electrode 2 and the crucible a are moved downwardly to an open position. At this position, the spent crucible a must be removed, the electrodes, at least surfaces $S_1$ and $S_2$ thereof, must be cleaned, and a new crucible and sample must be inserted. The present invention specifically provides an automatic cleaning device for removing spent crucible a and for cleaning surfaces $S_1$ and $S_2$.

Figure 7B:
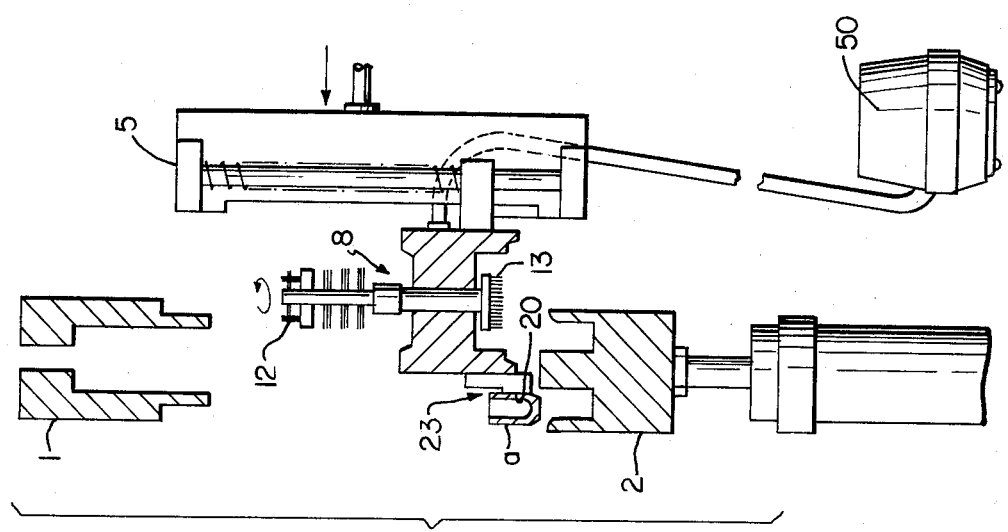
FIGS. 7(a) through 7(e) are sectional schematic views illustrating the sequence of operation of an extracting furnace including the automatic cleaning device of the present invention.

Thus, housing A includes a base 4. A support bracket 5 is laterally movable with respect to the electrodes 1, 2 along horizontal guide bars 6a, 6b which are fixed to base 4. This movement may be achieved, for example, by means of a hydraulic or air cylinder 7. The support bracket fixedly mounts a pair of vertical guide bars 9a, 9b. A cleaning unit 8 is vertically movable along guide bars 9a, 9b and is urged downwardly therealong by the force of gravity and by means of springs, such as compression springs 10. The cleaning unit 8 is transversely movable by means of support bracket 5 between a first position at a location laterally of electrodes 1 and 2, see FIG. 7(e), and a closed position at a location between electrodes 1 and 2, as shown in FIG. 1. In the second position of cleaning unit 8, upward movement of lower electrode 2 by means of cylinder 3 will cause lower electrode 2 to push cleaning unit 8 upwardly toward electrode 1 along vertical guide bars 9a, 9b. When lower electrode 2 is lowered by contracting cylinder 3, springs 10 and gravity will cause cleaning unit 8 to move downwardly to the position shown in FIG. 1.

Figure 4:
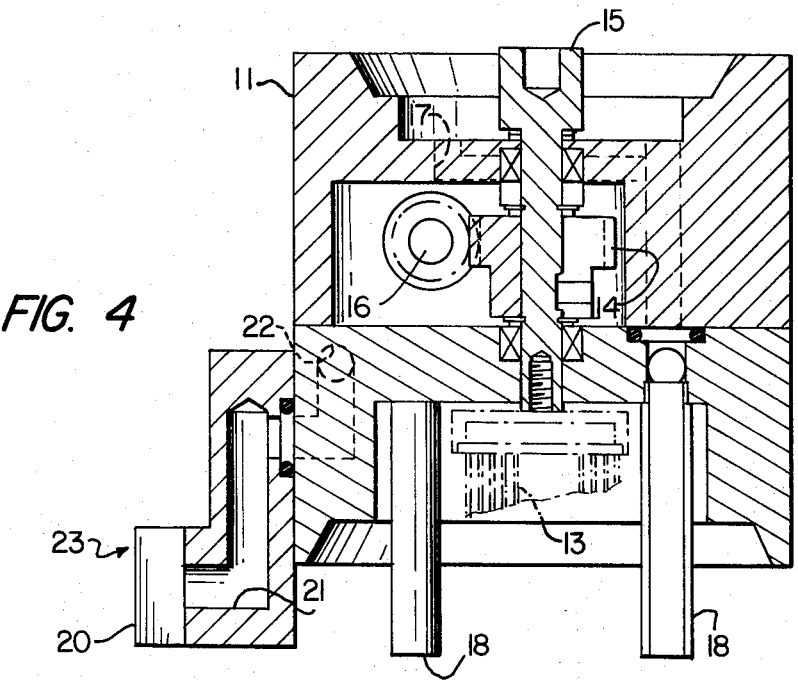
FIG. 4 is a section, on an enlarged scale, of the cleaning unit of the cleaning device, and particularly illustrating the internal structure of the cleaning unit.
Figure 5:
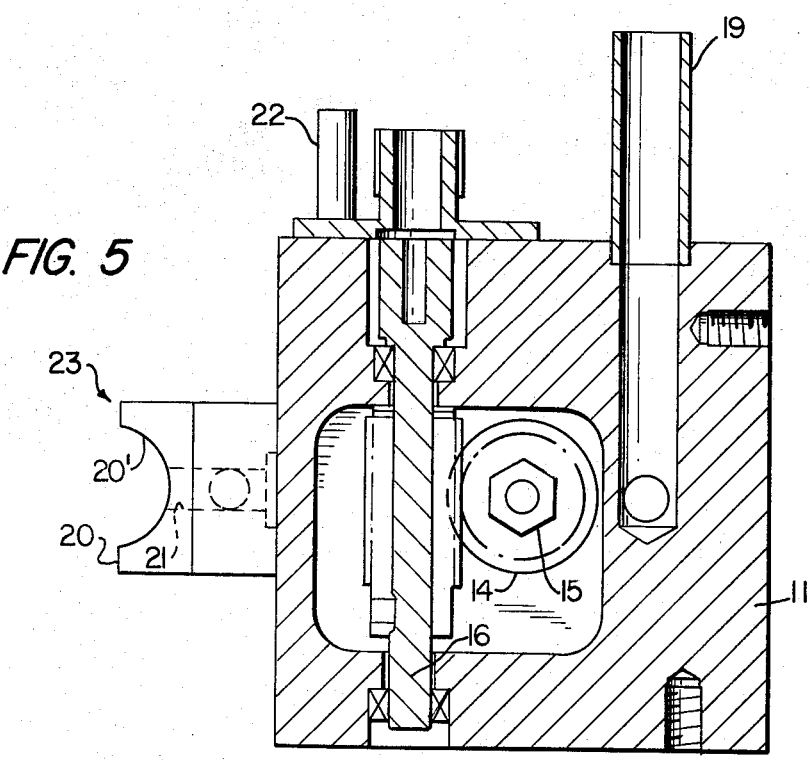
FIG. 5 is a horizontal cross-section of the arrangement of FIG. 4.
Figure 6:
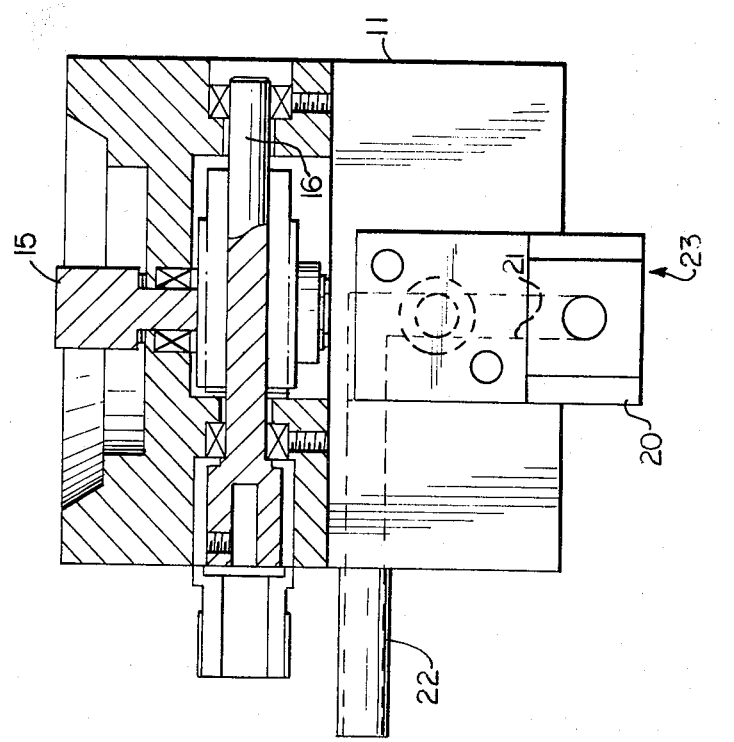
FIG. 6 is a partial vertical cross-section, taken substantially at a right angle to the plane of FIG. 4.

As shown in FIGS. 1-6, and particularly in FIGS. 4-6, cleaning unit 8 includes a gear block 11. For sake of clarity of illustration, the interior structure of gear block 11 is not shown in FIG. 1, but is shown in FIGS. 4-6. Gear block 11 may include two block members as illustrated, such members being detachably connected in a conventional manner, for example by mean of bolts. A vertical spindle 15 is journalled for rotation within gear block 11 and has fixed to the periphery thereof a first gear, for example worm gear 14. A horizontal shaft 16 is journalled for rotation within gear block 11 and is adapted to be connected to a power source, for example a flexible shaft (not shown) to achieve rotation of shaft 16. Shaft 16 has fixed thereto a second gear meshing with gear 14. In the illustrated arrangement, shaft 16 is a worm shaft engageable with worm gear 14. Rotation of shaft 15 will result in rotation of spindle 15 which has attached to opposite ends thereof upper and lower brushes 12, 13. Preferably, such brushes are freely and interchangeably threaded into the opposite ends of spindle 15.

During cleaning of electrode surfaces $S_1$ and $S_2$ by means of brushes 12 and 13, respectively, dust is generated, and a particularly important feature of the present invention involves a manner for removal of such dust. Specifically, a suction connection 19 is adapted to be connected to internal conduits of gear block 11, such conduits including a conduit 17 opening upwardly of gear block 11 and nozzles or conduits extending downwardly from and opening downwardly of gear block 11. With particular reference to FIG. 7(d), it will be apparent that the upper and lower electrodes have flanges which abut with gear block 11 during a cleaning operation, thereby forming upper and lower enclosed chambers. Conduits 17 and 18 open into the upper and lower closed chambers, respectively, and thereby remove dust generated during the cleaning operations by brushes 12 and 13, respectively. Connection 19 may be connected to any conventional or available source of suction, for example a vacuum cleaner 50 [(FIG. 7(b)].

Additionally, the cleaning device includes an arrangement for removing a spent crucible a from the electrodes upon movement of cleaning unit 8 to the second position thereof, i.e. between the electrodes. Thus, such removal structure 23 includes a crucible holder 20 mounted on cleaning unit 8. Holder 20 has a concave surface 20' generally corresponding to the external profile of crucible a. Holder 20 is preferably mounted at the lower portion of the front surface of gear block 11. A suction conduit 21 opens into concave surface 20' and is connected to a suction conduit 22 extending through gear block 11 and adapted to be connected to a source of suction, for example vacuum cleaner 50. Suction through conduits 22, 21 enables holder 20 to grasp crucible a until the crucible is removed to a position exterior of the electrodes, whereafter the suction may be terminated and the crucible may be discharged. Although the illustrated and preferred arrangement of the crucible removal device includes holder 20 capable of grasping the crucible by means of suction, further and other crucible removal devices may be employed. Thus, there may be provided an arrangement, for example associated with the cleaning unit 8, for removing crucible a by means of compressed air. Further, it would be possible to remove crucible a merely by contact by the cleaning unit upon advancement thereof to the second position thereof.

To facilitate automatic operation of the device of the invention, there may be provided devices for initiating the movement of cylinders 3 and 7. One such arrangement is illustrated in the drawings as including limit switch $LS_1$ for detecting the lower limit position of cleaning unit 8. This is achieved by limit switch $LS_1$ being contacted by slide block 24 which is fixedly mounted on gear block 11. A further limit switch $LS_2$ is mounted to be contacted by a spent or consumed crucible a upon the crucible being delivered to the removed position thereof.

The operation of the present invention, including the exemplary limit switches discussed above, will now be described in detail.

Figure 7A:
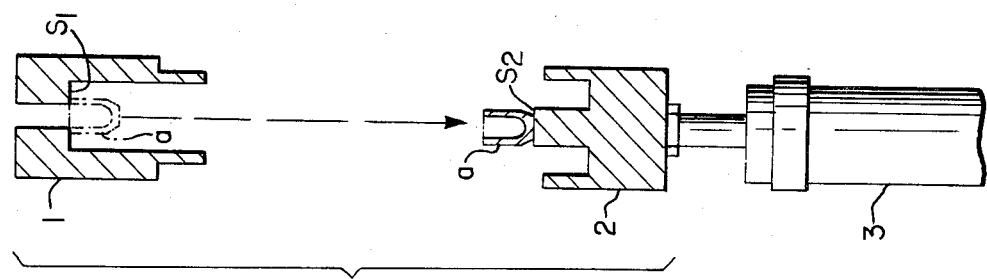
Figure 7E:
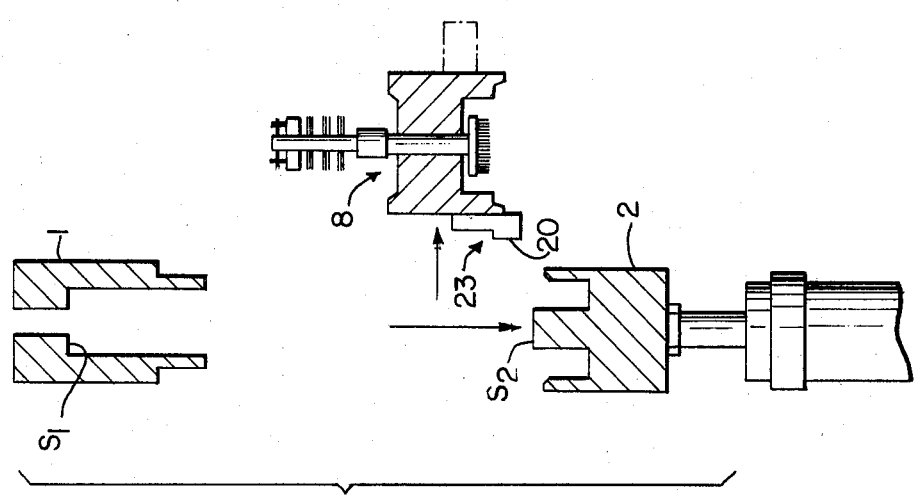
Figure 7D:
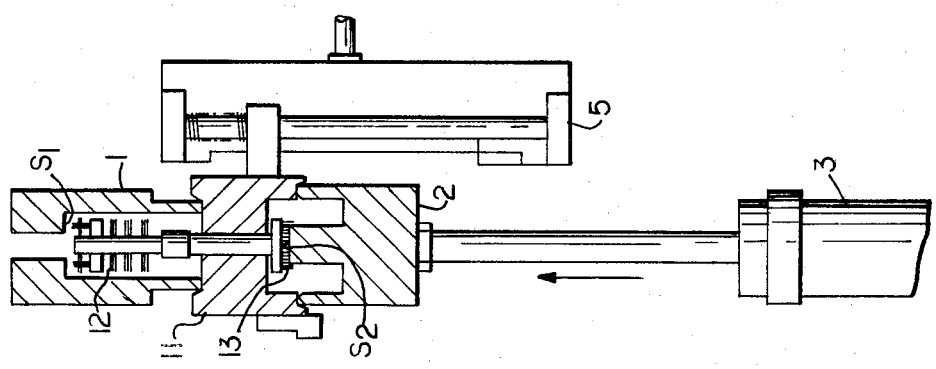
Figure 7C:
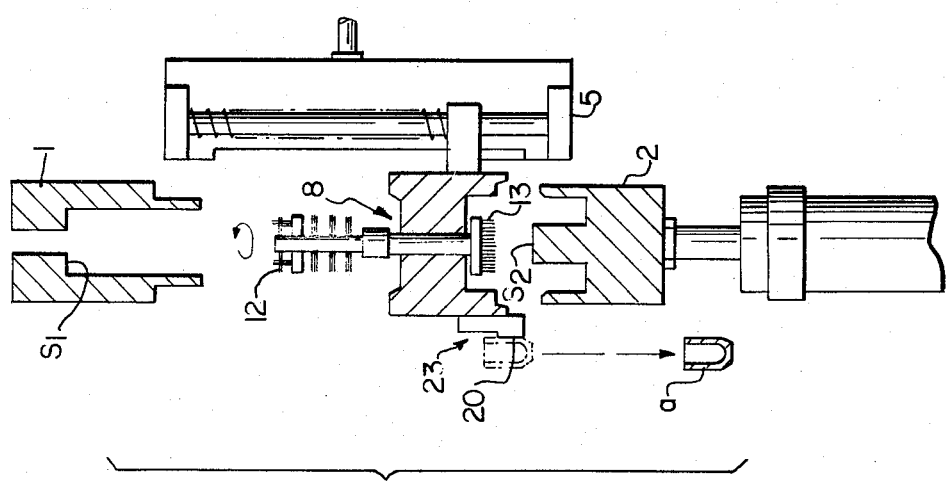

Upon the completion of a gas analyzing operation, air cylinder 3 is contracted, as shown in FIG. 7(a) to move lower electrode 2 and spent crucible a downwardly. Cylinder 7 is then extended to move support bracket 5 and cleaning unit 8 toward the second position thereof. During this movement, suction is applied to conduits 22, 21 such that holder 20 grasps the spent crucible a supported on electrode surface $S_2$, whereby further movement of cleaning unit 8 to the second position thereof results in the spent crucible being moved outwardly of the electrodes to a discharged position. When the cleaning unit 8 reaches the second position thereof, suction to conduits 22, 21 is terminated, such that the spent crucible is released and discharged, see FIG. 7(c). The movement of the spent crucible a to the discharged position thereof actuates limit switch $LS_2$, thereby causing cylinder 3 to be extending to raise lower electrode 2. Lower electrode 2 contacts cleaning unit 8 and moves cleaning unit 8 upwardly along vertical guide bars 9a, 9b against the force of springs 10 until the upper surface of gear block 11 contacts upper electrode 1. Brushes 12, 13 are continually rotated and then clean electrode surfaces $S_1$, $S_2$, as shown in FIG. 7(d). Dust generated during this cleaning operation is removed by suction via 19, 18, 17. Thereafter, cylinder 3 is contracted, thereby lowering lower electrode 2. Springs 10 and gravity cause cleaning unit 8 to move downwardly until block 24 actuates limit switch $LS_1$, thereby causing cylinder 7 to contract and move support bracket 5 and cleaning unit 8 laterally to the first position thereof, see FIG. 7(e). This completes a cleaning cycle, and the furnace is ready for the next analysis operation.

According to the present invention, a consumed crucible can be automatically removed, and both the upper electrode and the lower electrode can be automatically cleaned. Thus, the workload and burden on the persons in charge of the analysis operation can be reduced. Additionally, the quality of the cleaning operation is not influenced by different personnel in charge of cleaning.

Furthermore, the working environment can be prevented from become worsened due to dust generated during the cleaning operation, because the dust is removed by suction.

A further advantage of the present invention is that no additional power source is required for moving the cleaning unit upwardly and downwardly, since movement of the lower electrode moves the cleaning unit upwardly, and since the cleaning unit is moved downwardly by gravity and springs. Thus, the present invention provides the additional advantage of economy by not requiring an additional power source.

Although the present invention has been described and illustrated with respect to a preferred embodiment of the present invention, it is to be understood that various modifications may be made to the structure specifically described and illustrated without departing from the scope of the present invention.

What is claimed is:

1. In an extracting furnace for use with a gas analyzing device, said furnace being of the type including upper and lower electrodes relatively movable between a closed position, whereat a crucible containing a sample to be analyzed may be contacted and heated by said upper and lower electrodes, and an open position, whereat said upper and lower electrodes are spaced from each other, the improvement comprising an automatic cleaning device for cleaning said upper and lower electrodes when said electrodes are in said open position, said cleaning device comprising:

a support bracket mounted for movement laterally of said electrodes;

a cleaning unit supported on said support bracket and movable thereby between a first position located laterally of said electrodes and a second position located between said electrodes;

crucible removal means on said cleaning unit for removing a spent crucible from said electrodes upon movement of said cleaning unit to said second position thereof;

said cleaning unit including upper and lower cleaning elements operable for cleaning said upper and lower electrodes; and said cleaning unit being mounted on said support bracket for vertical movement relative thereto, such that when said cleaning unit is in said second position thereof, relative movement between said upper and lower electrodes toward said closed position thereof moves said cleaning unit vertically until said upper and lower cleaning elements are contacted with and clean said upper and lower electrodes.

2. The improvement claimed in claim 1, further comprising means for removing dust generated during cleaning of said upper and lower electrodes.

3. The improvement claimed in claim 2, wherein said dust removing means comprise conduits, adapted to be connected to a suction source, opening into areas above and below said cleaning unit.

4. The improvement claimed in claim 3, wherein said upper and lower electrodes have extending therefrom flanges contacting said cleaning unit, thereby forming upper and lower closed chambers, and said conduits extend through said cleaning unit and open into said upper and lower chambers.

5. The improvement claimed in claim 1, wherein said upper and lower electrodes have respective inner electrode surfaces, and said upper and lower cleaning elements comprise upper and lower brushes adapted to rotate against respective said electrode surfaces.

6. The improvement claimed in claim 5, further comprising means for rotating said brushes.

7. The improvement claimed in claim 6, wherein said cleaning unit includes a gear block, and said rotating means comprises a vertically extending spindle journalled for rotation in said gear block and supporting at opposite ends thereof said brushes, said spindle having fixed thereto a first gear, and a horizontally extending shaft journalled for rotation in said gear block and adapted to be connected to a power source for rotation thereof, said shaft having fixed thereto a second gear meshing with said first gear.

8. The improvement claimed in claim 7, wherein said first and second gears are worm gears.

9. The improvement claimed in claim 7, wherein said upper and lower brushes are removably threaded onto said opposite ends of said spindle.

10. The improvement claimed in claim 1, wherein said support bracket is slidably mounted on at least one horizontally extending guide bar, and further comprising means for moving said support bracket toward and away from said electrodes.

11. The improvement claimed in claim 10, wherein said upper electrode is fixed and said lower electrode is vertically movable toward and away from said upper electrode toward said closed and open positions, respectively.

12. The improvement claimed in claim 11, wherein said cleaning unit is slidably mounted on at least one vertically extending guide bar which is fixedly mounted on said support bracket, and further comprising spring means mounted on said vertically extending guide bar for urging said cleaning unit downwardly.

13. The improvement claimed in claim 1, wherein said crucible removal means comprises a crucible holder mounted on said cleaning unit, said holder having a concave surface substantially corresponding to the exterior profile of a crucible employed, and a conduit, adapted to be connected to a suction source, opening into said concave surface.

14. The improvement claimed in claim 13, wherein said conduit extends through said cleaning unit.

15. For use in an extracting furnace of a gas analyzing device, the furnace being of the type including upper and lower electrodes relatively movable between a closed position whereat a crucible containing a sample to be analyzed may be contacted and heated by the electrodes, and an open position whereat the electrodes are spaced from each other, an automatic cleaning device for cleaning the upper and lower electrodes when the electrodes are in the open position thereof, said cleaning device comprising:

a support bracket adapted to be mounted for movement laterally of the electrodes;

a cleaning unit supported on said support bracket and movable thereby between a first position located laterally of the electrodes and a second position located between the electrodes;

crucible removal means on said cleaning unit for removing a spent crucible from the electrodes upon movement of said cleaning unit to said second position thereof;

said cleaning unit including upper and lower cleaning elements operable for cleaning the upper and lower electrodes; and said cleaning unit being mounted on said support bracket for vertical movement relative thereto, such that when said cleaning unit is in said second position thereof, relative movement between the upper and lower electrodes toward the closed position thereof moves said cleaning unit vertically until said upper and lower cleaning elements are contacted with and clean the upper and lower electrodes.

16. A cleaning device as claimed in claim 15, further comprising means for removing dust generated during cleaning of the upper and lower electrodes.

17. A cleaning device as claimed in claim 16, wherein said dust removing means comprise conduits, adapted to be connected to a suction source, opening into areas above and below said cleaning unit.

18. A cleaning device as claimed in claim 17, wherein the upper and lower electrodes have extending therefrom flanges adapted to contact said cleaning unit, thereby forming upper and lower closed chambers, and said conduits extend through said cleaning unit and open into said upper and lower chambers.

19. A cleaning unit as claimed in claim 15, wherein the upper and lower electrodes have respective inner electrode surfaces, and said upper and lower cleaning elements comprise upper and lower brushes adapted to rotate against respective electrode surfaces.

20. A cleaning device as claimed in claim 19, further comprising means for rotating said brushes.

21. A cleaning device as claimed in claim 20, wherein said cleaning unit includes a gear block, and said rotating means comprises a vertically extending spindle journalled for rotation in said gear block and supporting at opposite ends thereof said brushes, said spindle having fixed thereto a first gear, and a horizontally extending shaft journalled for rotation in said gear block and adapted to be connected to a power source for rotation thereof, said shaft having fixed thereto a second gear meshing with said first gear.

22. A cleaning device as claimed in claim 21, wherein said first and second gears are worm gears.

23. A cleaning device as claimed in claim 21, wherein said upper and lower brushes are removably threaded onto said opposite ends of said spindle.

24. A cleaning device as in claim 15, wherein said support bracket is slidably mounted on at least one horizontally extending guide bar, and further comprising means for moving said support bracket toward and away from the electrodes.

25. A cleaning unit as claimed in claim 24, wherein the upper electrode is fixed and the lower electrode is vertically movable toward and away from the upper electrode toward the closed and open positions, respectively, said cleaning unit is slidably mounted on at least one vertically extending guide bar which is fixedly mounted on said support bracket, and further comprising spring means mounted on said vertically extending guide bar for urging said cleaning unit downwardly.

26. A cleaning device as claimed in claim 15, wherein said crucible removal means comprises a crucible holder mounted on said cleaning unit, said holder having a concave surface substantially corresponding to the exterior profile of a crucible employed, and a conduit, adapted to be connected to a suction source, opening into said concave surface.

27. A cleaning device as claimed in claim 26, wherein said conduit extends through said cleaning unit.

* * * * *